(12) United States Patent  
Shakur (10) Patent No.: US 11,647,929 B2  
(45) Date of Patent: May 16, 2023

(54) ECG DEVICE

(71) Applicant: Cambridge Heartwear Limited, Cambridge (GB)

(72) Inventor: Rameen Shakur, Cambridge (GB)

(73) Assignee: CAMBRIDGE HEARTWEAR LIMITED, Cambridge (GB)

( * ) Notice: Subject to any disclaimer, the term of this patent is extended or adjusted under 35 U.S.C. 154(b) by 809 days.

(21) Appl. No.: 15/841,719

(22) Filed: Dec. 14, 2017

(65) Prior Publication Data

US 2019/0183369 A1    Jun. 20, 2019

(51) Int. Cl.
*A61B 5/25* (2021.01)
*A61B 5/00* (2006.01)
(Continued)

(52) U.S. Cl.
CPC ............ *A61B 5/25* (2021.01); *A61B 5/14542* (2013.01); *A61B 5/282* (2021.01); *A61B 5/30* (2021.01);
(Continued)

(58) Field of Classification Search
CPC . A61B 5/0408; A61B 5/04085; A61B 5/0428; A61B 5/0452; A61B 5/14542; A61B 5/6823; A61B 5/6831; A61B 2560/0425; A61B 2562/0219; A61B 2562/0271; A61B 2562/04; A61B 5/0006; A61B 5/6841; A61B 5/25; A61B 5/349; A61B 5/318; A61B 5/30; A61B 5/282; A61B 5/322; A61B 5/305; A61B 5/28; B23P 19/04

See application file for complete search history.

(56) References Cited

U.S. PATENT DOCUMENTS 6,560,473 B2 * 5/2003 Dominguez ............ A61B 5/282  
600/382  
10,602,942 B2    3/2020 Shakur  
(Continued)

OTHER PUBLICATIONS

International Search Report and Written Opinion dated Mar. 28, 2019 for corresponding International Application No. PCT/GB2018/053637.

(Continued)

*Primary Examiner* — Adam Z Minchella  
(74) *Attorney, Agent, or Firm* — Hamilton, Brook, Smith & Reynolds, P.C.

(57) ABSTRACT

We disclose a portable wearable device for measuring electrocardiographic signals, the device comprising a first portion comprising at least two electrodes; a second portion comprising at least three electrodes; the first portion and the second portion being vertically spaced from one another; a controller configured to take: a first potential difference measurement using one of the electrodes of the first portion and one of the electrodes of the second portion; a second potential difference measurement using one other of the electrodes of the first portion and one other of the electrodes of the second portion; and a third potential difference measurement using one other of the electrodes of the first portion and one other of the electrodes of the second portion. The controller is configured to simultaneously take the first, second and third potential difference measurements at three independent positions of a user's body.

26 Claims, 6 Drawing Sheets

(51) Int. Cl.
  *A61B 5/30* (2021.01)
  *A61B 5/282* (2021.01)
  *A61B 5/318* (2021.01)
  *A61B 5/349* (2021.01)
  *A61B 5/145* (2006.01)
  *B23P 19/04* (2006.01)

(52) U.S. Cl.
  CPC .............. *A61B 5/318* (2021.01); *A61B 5/349* (2021.01); *A61B 5/6823* (2013.01); *A61B 5/6831* (2013.01); *B23P 19/04* (2013.01); A61B 2560/0425 (2013.01); A61B 2562/0219 (2013.01); A61B 2562/0271 (2013.01); A61B 2562/04 (2013.01)

(56) References Cited

U.S. PATENT DOCUMENTS

| | | | |
|---|---|---|---|
| 11,013,470 | B2 | 5/2021 | Shakur |
| 2003/0176795 | A1 | 9/2003 | Harris |
| 2008/0154100 | A1 | 6/2008 | Burnes |
| 2008/0154110 | A1* | 6/2008 | Burnes ................... A61B 5/282 600/382 |
| 2009/0076363 | A1* | 3/2009 | Bly ......................... A61B 5/361 600/372 |
| 2009/0112110 | A1 | 4/2009 | Zhang |
| 2011/0160601 | A1* | 6/2011 | Wang ..................... A61B 5/6841 600/509 |
| 2011/0288605 | A1* | 11/2011 | Kaib ...................... A61B 5/7221 607/5 |
| 2012/0108917 | A1* | 5/2012 | Libbus ................... A61B 5/002 705/2 |
| 2012/0179055 | A1 | 7/2012 | Tamil |
| 2015/0164349 | A1 | 6/2015 | Gopalakrishnan |
| 2016/0029913 | A1* | 2/2016 | Smith ..................... A61B 5/316 600/523 |
| 2016/0232340 | A1 | 8/2016 | Feng |
| 2016/0302726 | A1* | 10/2016 | Chang .................... A61B 5/259 |
| 2018/0020931 | A1* | 1/2018 | Shusterman ....... A61B 5/02116 600/483 |
| 2019/0015008 | A1* | 1/2019 | Alizadeh ............... A61B 5/282 |
| 2019/0099162 | A1 | 4/2019 | Keshet |

OTHER PUBLICATIONS

Bai, S., et al., "Convolutional Sequence Modeling Revisited," Workshop track—ICLR (2018).

Kiranyaz, S., et al., "Real-Time Patient-Specific ECG Classification by 1-D Convolutional Neural Networks," IEEE Transactions on Biomedical Engineering, vol. 63, No. 3 (Feb. 16, 2016).

Patel, A., et al., "Real Time ECG Feature Extraction and Arrhythmia Detection on a Mobile Platform," International Journal of Computer Applications, vol. 44, No. 23, p. 0975-8887 (Apr. 2012).

\* cited by examiner

ECG DEVICE

TECHNICAL FIELD OF THE DISCLOSURE

The disclosure relates to a portable electrocardiograph (ECG) monitoring device.

BACKGROUND OF THE DISCLOSURE

Electrocardiograph (ECG) monitors are widely used to obtain medical (i.e. biopotential) signals containing information indicative of the electrical activity associated with the heart and any underlying pathology. To obtain medical signals, ECG electrodes are applied to the skin of a patient in various locations. The electrodes, after being positioned on the patient, connect to an ECG monitor by a set of ECG lead wires. The distal end of the ECG lead wire, or portion closest to the patient, may include a connector which is adapted to operably connect to the electrode to receive medical signals from the body. The proximal end of the ECG lead set is operably coupled to the ECG monitor and supplies the medical signals received from the body to the ECG monitor.

Generally speaking, if we want to take an ECG as someone is going about their daily business (rather than at rest), we need to use a device called a Holter monitor. This requires fixing 12 leads on to the patient's chest and carrying around this cumbersome device that only has a few hours' power. To fit a Holter monitor you may need to be referred by your general physician to a cardiology department, which could mean a wait to obtain an appointment. Then you need to have that data interpreted—it could be more than a month-and-a-half between the decision to take an ECG and actually having a diagnosis as to the underlying cardiac pathology. The data is provided from the Holter monitor but due to the uncomfortable and non-ergonomic design, the patients are reluctant to wear the device for the necessary long periods to identify any intermittent or transient pathologies. Furthermore, it is also a very expensive piece of equipment. In addition, the data generated by the Holter monitor are not accessible in real time to provide a diagnosis.

SUMMARY OF THE DISCLOSURE

The present disclosure addresses the problems associated with ECG devices. The present disclosure proposes a wearable ECG device which is capable of providing real-time data for heart rhythms in three individual or unique positions around the heart of a user. There are no leads, so it is much more comfortable to wear and easy to fit. Everything is enclosed in a (e.g. waterproof) casing, so it is very robust and the data produced is much more sensitive. The casing is generally flexible and malleable made with, for example, silicon. Particularly the casing is ergonomically designed to be fitted at the chest of both male and female users. The ECG device is paired with a smart device through for example a wireless connection (or Bluetooth connection). The ECG waves can be viewed on a dedicated smart device application in real time. The data can also be wirelessly streamed in real time to the cloud where the use of new algorithms and artificial intelligence is able to identify aberrant rhythms just as a physician would.

According to one aspect of the present disclosure, there is provided a portable device for measuring electrocardiographic signals, the device comprising:

a first portion comprising at least two electrodes;

a second portion comprising at least three electrodes; the first portion and the second portion being vertically spaced from one another;

a controller configured to take:
  a first potential difference measurement using one of the electrodes of the first portion and one of the electrodes of the second portion;
  a second potential difference measurement using one other of the electrodes of the first portion and one other of the electrodes of the second portion; and
  a third potential difference measurement using one other of the electrodes of the first portion and one other of the electrodes of the second portion;
wherein the controller is configured to simultaneously take the first, second and third potential difference measurements at three independent positions of the body of a user.

The controller may be configured to simultaneously generate: a first electrocardiographic waveform from the first potential difference measurement; a second electrocardiographic waveform from the second potential difference measurement; and a third electrocardiographic waveform from the third potential difference measurement.

Typically, portable ECG devices do not take three independent measurements from three different locations near the heart at the same time. The ECG device of the present disclosure measures potential differences from three different anatomically significant locations and therefore generates three independent corresponding ECG waveforms. The at least three measurements maximize the potential output of the waveforms. In other words, it is possible to amplify the peaks of the individual ECG signals for each measurement. Therefore, it is possible to maximize potential difference output to achieve more accurate and sensitive ECG data for abnormalities defining an underlying rhythm. By optimizing each measurement (e.g., by filtering noise to signal ratios), the device is configured to take the optimum possible output for each measurement. The device then takes at least three independent measurements which are particularly advantageous for defining the underlying rhythm of the heart. This way, the detection of abnormalities in heart conditions can be detected with a higher degree of sensitivity and specificity.

The device may be positioned such that the first portion of the device is located near a region proximal to a sinoatrial node of a heart of the body of the user and the second portion is located near a region close to the apex and ventricular area of the heart of the user. It will be appreciated that the sensors or detectors of the first portion of the device are located near the top region of the heart from where electrical signals begin to generate and travel towards a bottom region (towards the apex of the heart). The sensors or detectors of the second portion of the device are spread in the second portion and located towards the bottom region of the heart which is near the apex or base of the heart. It is apparent that the sensors of the first and second portions are all located along the direction where electrical signals flow in the heart, and as a result, sensitive and accurate ECG measurements data can be obtained.

The controller may be configured to take: the first potential difference measurement using a first electrode of the first portion and a first electrode of the second portion; the second potential difference measurement using a second electrode of the first portion and a second electrode of the second portion; and the third potential difference measurement using the second electrode of the first portion and a third electrode of the second portion. It will be appreciated that other combination of electrodes can also be used to obtain the at least three independent simultaneous measurements. For example, the first potential difference can be measured using the first sensor of the first portion and the second sensor of the second portion. Similarly, the second potential difference can be measured using the second sensor of the first portion and the first sensor of the second portion. Other combination of sensors from the first and second portions of the device could be combined to take the at least three measurements.

The electrodes of the first portion of the device may be laterally spaced from one another. The first and second electrodes of the first portion are generally located on the left and right sides of the first portion of the device. The electrodes of the first portion generally have a lateral distance of about 20 mm to about 80 mm. Other suitable distances can also be contemplated for optimization of the ECG amplitudes.

The electrodes of the second portion of the device may be laterally spaced from one another. The distance between the electrodes of the second portion may be from about 20 mm to 80 mm. For such distance ranges, an improved ECG peak with amplified and accurate waves is achieved. However, the disclosure is not restricted to this distance range only, other suitable distances can be contemplated.

The first portion and the second portion of the device may be integrated portions within the device. In other words, the first portion or the top portion and the second portion or the bottom portion form part of the device. The device may further comprise a connector portion between the first and second portions of the device. In one example, the connector portion is made of a flexible inert material. The flexible material is generally hypoallergenic material. The flexible connector portion may be shaped to have a pre-determined width or diameter from about 2 mm to about 9 mm. Advantageously, this width or diameter range is specifically chosen so that the device can be comfortably fitted behind the bridge of bra cups for a female user.

The second portion of the device may comprise a first section and a second section, and wherein the first section comprises the at least three detectors.

The second section of the second portion of the device may be positioned at a predetermined angle in respect of a longitudinal surface of the first portion of the device. The pre-determined angle may be from about 15° to 35°. Advantageously, this angle of the second section enables the device to be fitted easily behind or underneath the breast of a female user.

The first and second portions of the device may comprise a plurality of flexible regions. Advantageously, these flexible regions enable the device to flex and mold itself around the thorax as necessary. The flexibility of the device enables it to be in constant contact with the skin of the body of the user, which enables more consistent measurements and results.

The device may comprise a temperature sensor which is configured to monitor a core skin temperature of the user. Here the core skin temperature is measured from a region proximal to the heart or lung of the user. Advantageously, the temperature is monitored from a more central region (e.g. lung or heart) of the body. Conventionally, the temperature is monitored from a peripheral region (e.g. ear) of the body. The temperature monitoring system of the present disclosure is more accurate because it monitors a temperature from a core region (e.g. lung or heart) of the body.

The device may comprise a pulse oximeter which is configured to monitor an oxygen saturation level from a region proximal to the heart or lung of the user. Conventional pulse oximeter devices monitor readings from a finger or a wrist of a user. These conventional devices have challenges in terms of accuracy in measurements. For example, when nail polish is used on the finger (which is located at the periphery of the body), the measurement accuracy of the conventional pulse oximeter can be affected. This can be overcome from the device of the present disclosure where oxygen saturation is measured near the core body area (e.g. near the lung or heart) which results in more accurate and sensitive oxygen saturation levels.

Furthermore, the pulse oximeter is generally located in a region of the device which is almost in constant contact with the body. In one example, the pulse oximeter can be located in the second section (e.g. the section which is distant from the detectors) of the second portion. Given that the second section of the second portion is designed or shaped in a predetermined angle, it is in constant contact with the skin. This arrangement is particularly advantageous for female users.

The device may further comprise wireless communication means. The device may have an energy source such as a battery, more preferably a rechargeable battery. The energy source of the device may have wireless charging capabilities. The device may further comprise an accelerometer. The accelerometer is particularly advantageous because it helps to define a distance of movement when undertaking any exercise or general activity, and also in the event of any acute pathology (e.g. an acute event such as an arrhythmic event) occurring, it can help to corroborate the abnormal pathology with patient's symptoms.

The device is generally over-molded by a suitable material such as silicon. In one example, the encapsulation material can be a waterproof hypo allergenic material. It will be appreciated that other types of suitable materials can be contemplated. Advantageously, the device is sealed by the encapsulating material, there is no scope for putting a socket or other connections from the outer packaging of the device. As a result, the device is robust and reliable for any conditions, particularly for use in outdoor conditions (e.g. used in sweating conditions or where there may be excessive perspiration or in lite water sports).

The device is generally tied or attached with the body through a strap strap-mechanism.

According to a further aspect of the present invention, there is provided a method of manufacturing a portable device for measuring electrocardiographic signals, the method comprising:
  forming a first portion comprising at least two electrodes;
  forming a second portion comprising at least three electrodes; the first portion and the second portion being vertically spaced from one another;
  providing a controller to take:
    a first potential difference measurement using one of the electrodes of the first portion and one of the electrodes of the second portion;
    a second potential difference measurement using one other of the electrodes of the first portion and one other of the electrodes of the second portion; and
    a third potential difference measurement using one other of the electrodes of the first portion and one other of the electrodes of the second portion;
  wherein the controller simultaneously takes the first, second and third potential difference measurements at three independent positions of a user's body.

BRIEF DESCRIPTION OF THE PREFERRED EMBODIMENTS

Some preferred embodiments of the disclosure will now be described by way of example only and with reference to the accompanying drawings, in which:

FIG. 6 (b) illustrates a schematic rear view of the assembled ECG device of FIG. 6 (a).

DETAILED DESCRIPTION OF THE PREFERRED EMBODIMENTS

Figure 1:
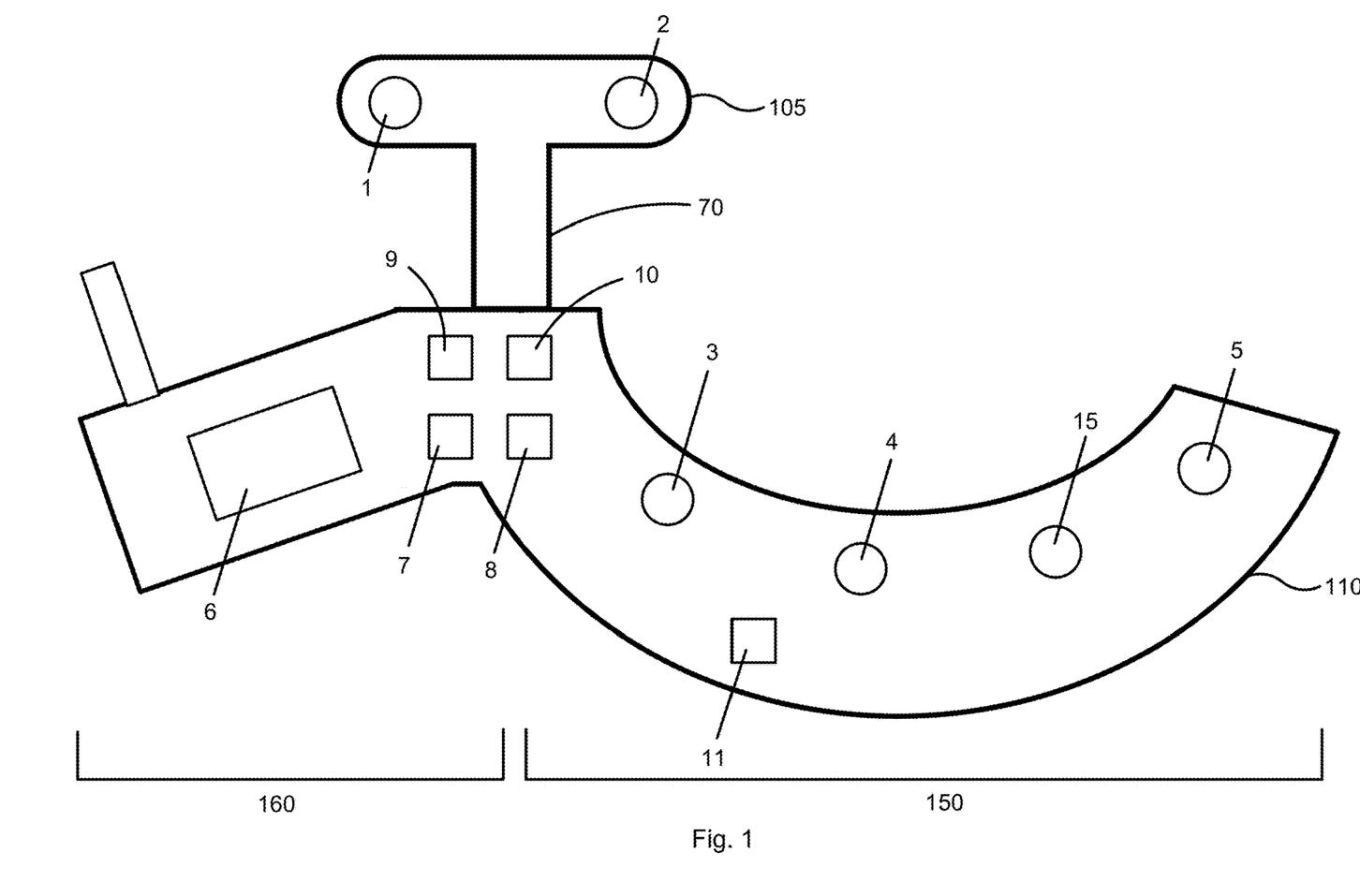
FIG. 1 illustrates a schematic representation of an exemplary ECG device according to one embodiment of the present disclosure.

FIG. 1 illustrates a schematic representation of an exemplary ECG device according to one embodiment of the present disclosure. The device has two portions: a first or top portion 105 and a second or bottom portion 110. There is a connection portion 70 between the first portion 105 and the second portion 110. The first portion 105 includes at least two ECG detectors 1, 2. These detectors 1, 2 are generally laterally distant from one another. The second portion 110 of the device has a first section 150 and a second section 160. The first section 150 generally includes at least three electrodes or detectors 3, 4, 5. In this instance, in the device of FIG. 1, there are four electrodes 3, 4, 5 and 15 in the second section 150 of the second portion 110.

The device of FIG. 1 can be generally positioned such that the first portion 105 of the device is located near a region proximal to a sinoatrial node of a heart (not shown) of the body of the user and the second portion is located near a region of an apex mitral area of the heart of the body of the user. It will be appreciated that the sensors or detectors 1,2 of the first portion 105 of the device are located near the top region of the heart from where electrical signals begin to generate and travel towards a bottom region (towards the apex of the heart). The sensors or detectors 3, 4, 5, 15 of the second portion 110 of the device are spread in the second portion and located towards the bottom region of the heart near the apex of the heart. It is apparent that the sensors of the first and second portions are all located along the direction where electrical signals flow in the heart, and as a result, sensitive and accurate ECG measurements data can be obtained.

In FIG. 1, the second section 160 can be positioned at a predetermined angle in respect of a longitudinal or main surface of the first portion 105 of the device. The predetermined angle may be from about 20° to 30°. Advantageously, this angle of the second section enables the device to be fitted easily behind or underneath the breast tissue of a female user. In one embodiment, the second section 160 includes a pulse oximeter 6. However, the pulse oximeter 6 can be located in any other location of the device.

The device of FIG. 1 includes a temperature sensor 11 which is capable of measuring a temperature from a region which is very near from the lung and/or heart of the body. The device also includes WIFI capability device 9, indicators 9, 10 and accelerometer 8. The locations of these devices are indicative only—they can be located in other places of the device.

The device of FIG. 1 also includes a plurality of flexible regions (not shown) in the second portion 110 of the device. The flexible regions enable the device to be fitted with the body. The connector 70 between the first portion 105 and the second portion 110 are made of flexible material. The connector 70 is shaped or designed to have a width or diameter of about 2 to 7 mm. This particular dimension range is designed so that the connector 70 can be placed very easily behind the bridge between bra-cups for female users.

Figure 2:
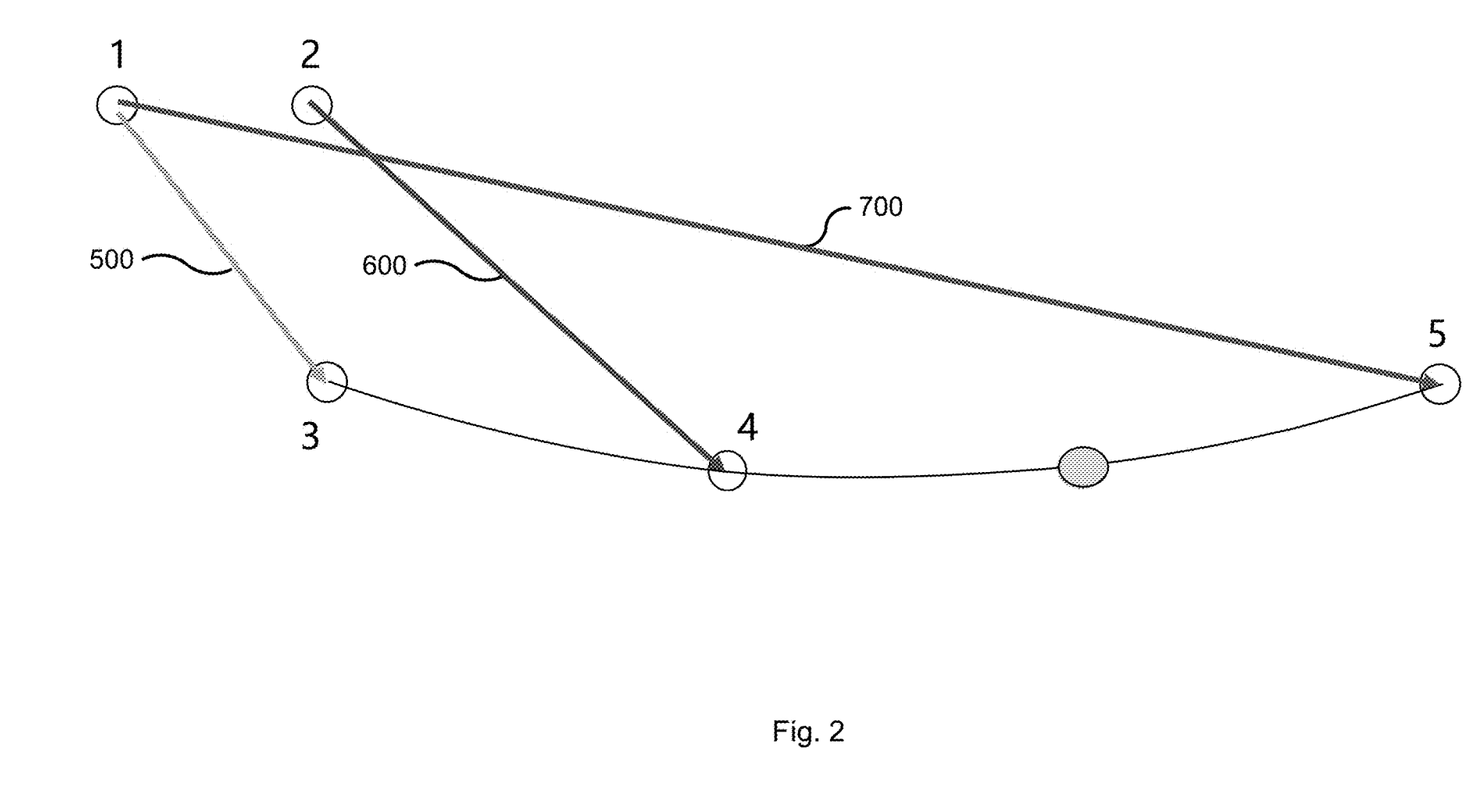
FIG. 2 illustrates a schematic representation of three independent measurements according to one embodiment of the present disclosure.

FIG. 2 illustrates a schematic representation of three independent measurements according to one embodiment of the present disclosure. In the examples, detectors 1 and 2 are located in the first portion 105 of the device and detectors 3, 4, 5 are located in the second portion 110 of the device. The first independent potential difference measurement 500 is taken using detectors 1 and 3. The second independent potential difference measurement 600 is taken using detectors 2 and 4. The third independent potential difference measurement 700 is taken using detectors 1 and 5. These three measurements 500, 600 and 700 are taken simultaneously from three different locations from the body.

Figure 3:
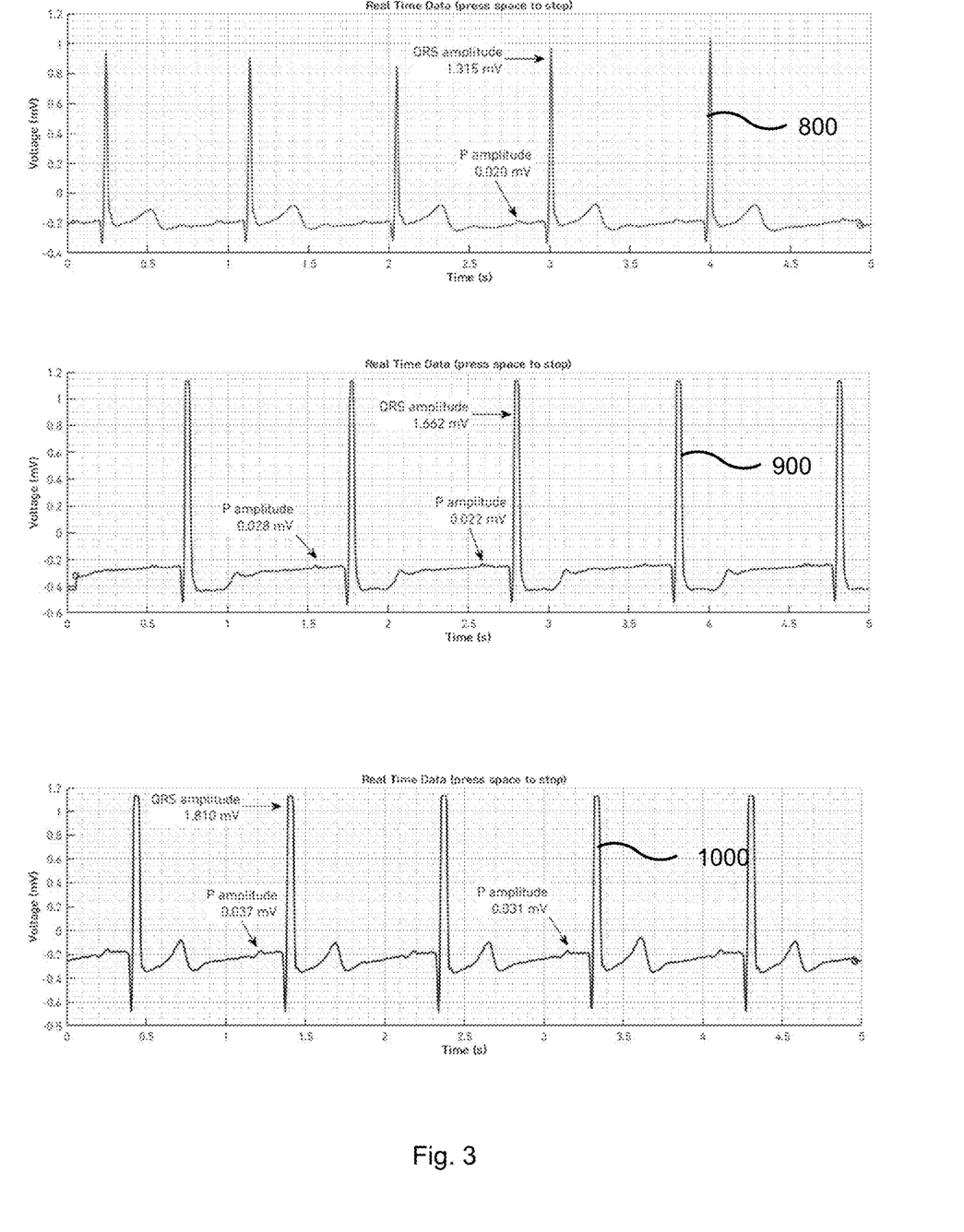
FIG. 3 illustrates the ECG waveforms generated from the three independent measurements of FIG. 2.

FIG. 3 illustrates the ECG waveforms generated from the three independent measurements of FIG. 2. In this example, waveform 800 corresponds to measurement 500 in FIG. 2, waveform 900 corresponds to measurement 600 and waveform 1000 corresponds to measurement 700 of FIG. 2. The advantage of three independent measurements is that p-waves are amplified which improves the likelihood of detection of irregularities in ECG signals. Because measurements are taken from three independent locations producing three independent waveforms, it is more effective in detection, e.g., of p-waves. The conventional devices do not take three different measurements at the same time and therefore it is much more difficult to detect the presence of p-waves in the ECG waveforms. This problem is overcome by the three independent measurements of the device of the present disclosure.

Figure 4:
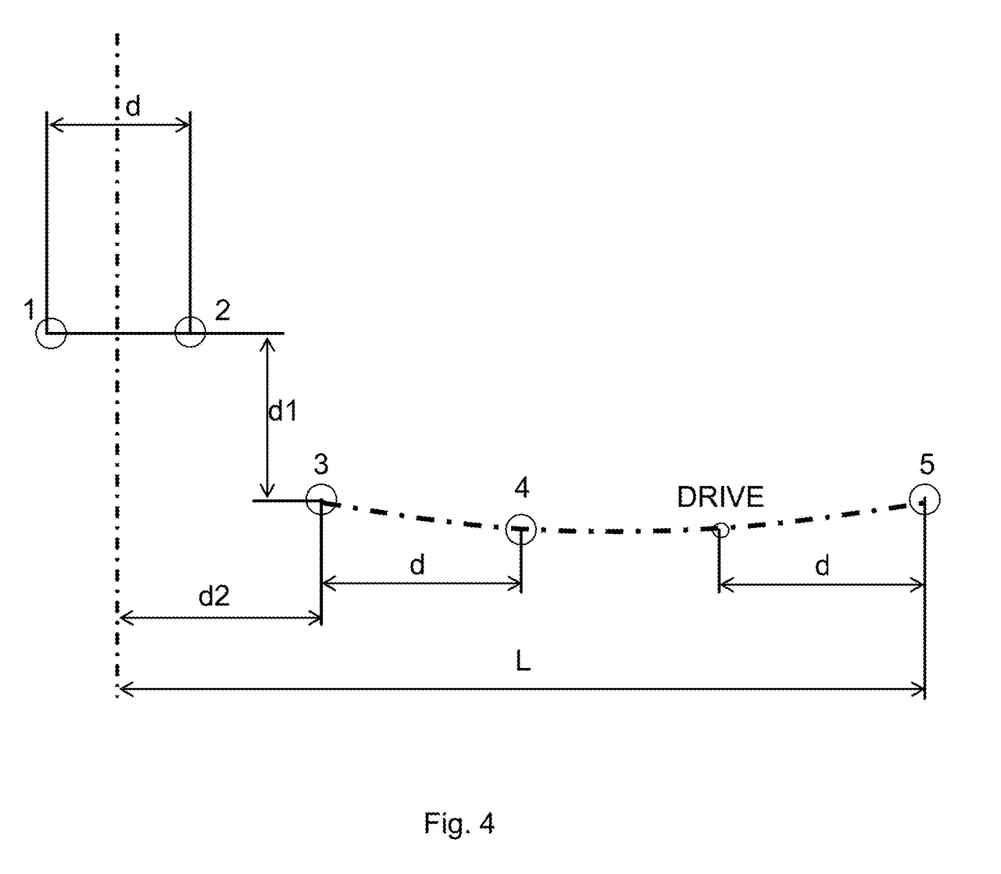
FIG. 4 illustrates a schematic representation of the arrangements of the detectors according to one example of the present disclosure.

FIG. 4 illustrates a schematic representation of the arrangements of the detectors according to one example of the present disclosure. The sensors in both the first and second portions are laterally spaced from one another. For example, the distance (d) between the detectors 1, 2 are of the first portion are about 20 mm to 80 mm. The lateral distance (d) between the detectors 3, 4, 5 are between about 20 mm to 80 mm. The vertical distance (d1) between the detectors of the first and second portions is about 20 mm to 80 mm. The distance (d2) between the middle point of the detectors 1, 2 and the first detector 3 of the second portion is about 20 mm to 80 mm. The distance (L) between the middle point of the detectors 1, 2 and the final detector 5 of the second portion is about 100 mm to about 250 mm Advantageously, the device provides improved ECG waveforms with amplified p-waves with these measurements. However, it will be appreciated that the invention is not restricted to these distances only. Other suitable distances can be contemplated.

Figure 5:
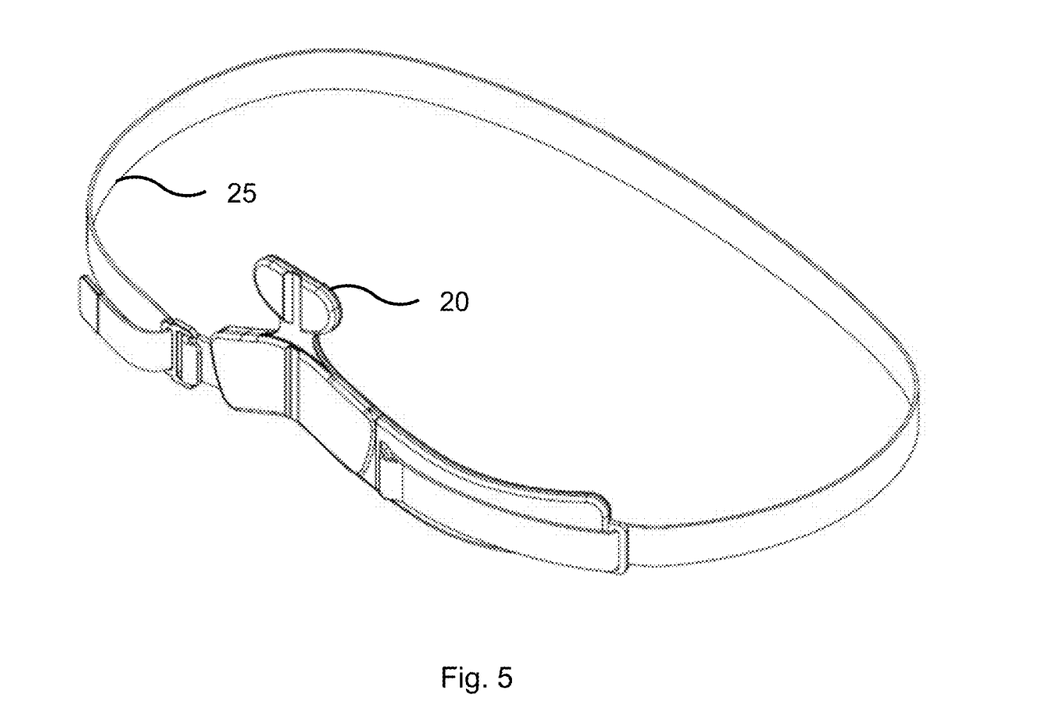
FIG. 5 illustrates a schematic assembled view of the ECG device according to one embodiment of the present disclosure.

FIG. 5 illustrates a schematic assembled view of the ECG device according to one embodiment of the present disclosure. The device assembly includes the ECG device 20 and a strap 25 attached to the device 20. The strap 25 is used to tie the device around the body of the user.

Figure 6A:
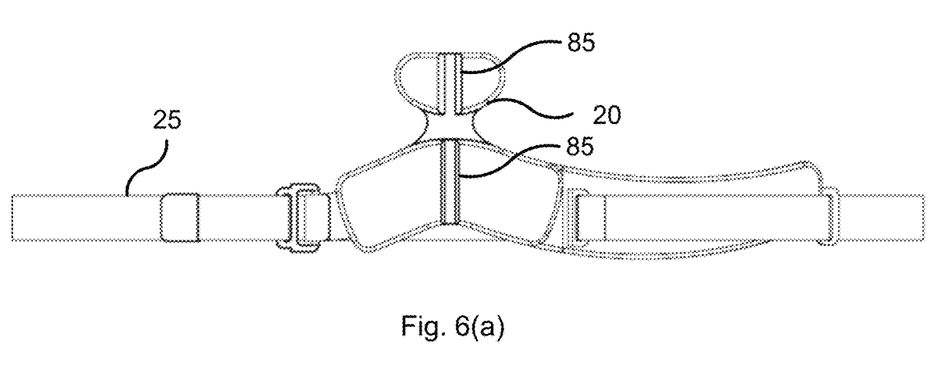
FIG. 6(a) illustrates a schematic front view of an assembled ECG device according to one embodiment of the present disclosure.

FIG. 6(*a*) illustrates a schematic front view of an assembled ECG device according to one embodiment of the present disclosure. The device 20 includes flexible portions 85 in the outer packaging of the device. The strap 25 is attached with a suitable strap mechanism. The invention is not restricted to the strap mechanism shown in the figure. Other suitable strap mechanisms can be used.

Figure 6B:
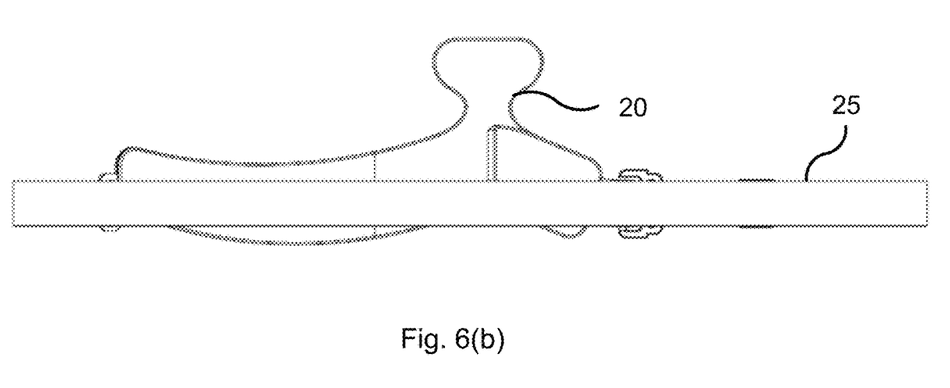

FIG. 6 (*b*) illustrates a schematic rear view of the assembled ECG device of FIG. 6 (*a*). The same reference numerals as FIG. 6 (*a*) are used.

Although the disclosure has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the disclosure, whether alone or in any appropriate combination with any other feature disclosed or illustrated herein.

The invention claimed is:

1. A portable device for measuring electrocardiographic signals, the device comprising:
  (a) a first portion comprising at least two ECG electrodes configured to cover a sinoatrial node of a user, the first portion defining an uppermost edge of the device;
  (b) a flexible second portion elongated in a substantially horizontal direction and being located below the first portion, comprising:
    (i) a heart apex mitral-covering first section comprising at least three ECG electrodes;
    (ii) a second section;
    (iii) the at least two ECG electrodes of the first portion being vertically higher than any of the other electrodes of the device; and
    (iv) at least a majority of the electrodes of the second portion being at a greater lateral distance from a vertically elongated line, as compared to a lateral distance between the vertically elongated line and the electrodes of the first portion;
  (c) a wireless communicator located between the heart apex mitral-covering first section and the second section, the vertical line extending through the wireless communicator,
  (d) a body core temperature sensor located between a pair of the at least two ECG electrodes of the first portion or the at least three ECG electrodes of the flexible second portion;
  (e) a controller configured to take:
    (i) a first potential difference measurement using one of the electrodes of the first portion and one of the electrodes of the second portion;
    (ii) a second potential difference measurement using one other of the electrodes of the first portion and one other of the electrodes of the second portion; and
    (iii) a third potential difference measurement using the one other of the electrodes of the first portion and a further one other of the electrodes of the second portion;
  wherein the controller is configured to simultaneously take the first, second and third potential difference measurements at three independent positions of a user's body;
  (f) a single strap for removably attaching the at least two ECG electrodes, the at least three ECG electrodes, and the temperature sensor in operating positions with all of the at least two ECG electrodes, the at least three ECG electrodes, and the temperature sensor being located where heart electrical signals flow, the single strap being a chest strap connected to only the second portion, and the first portion being spaced above a laterally extending line through the strap;
  (g) a distance between a middle point of the at least two electrodes of the first portion and at least one of the electrodes of the at least three electrodes of the second portion is between 20 mm and 80 mm; and
  (h) a distance between the middle point of the at least two electrodes of the first portion and another of the at least three electrodes of the second portion is between 100 mm and 250 mm.

2. The device according to claim 1, wherein the controller is configured to simultaneously generate:
  a first electrocardiographic waveform from the first potential difference measurement;
  a second electrocardiographic waveform from the second potential difference measurement; and
  a third electrocardiographic waveform from the third potential difference measurement.

3. The device according to claim 1, wherein the controller is configured to take:
  the first potential difference measurement using a first electrode of the first portion and a first electrode of the second portion;
  the second potential difference measurement using a second electrode of the first portion and a second electrode of the second portion; and
  the third potential difference measurement using the second electrode of the first portion and a third electrode of the second portion.

4. The device according to claim 1, wherein the electrodes of the first portion of the device are laterally spaced from one another.

5. The device according to claim 1, wherein the electrodes of the second portion of the device are laterally spaced from one another, and the first portion is part of a waterproof casing.

6. The device according to claim 5, wherein the distance between a pair of the electrodes of the second portion is from about 20 mm to 80 mm, and the second portion is waterproof encapsulated.

7. The device according to claim 1, wherein the first portion and at least part of the second portion of the device are integrated portions within the device.

8. The device according to claim 1, having a width and a curved shape that allows the portable device to be comfortably fitted behind a bridge of a bra cup for a female user.

9. The device according to claim 1, further comprising a flexible connector portion shaped to have a pre-determined width of about 2 mm to about 8 mm, the flexible connector portion vertically extending between the first and second portions of the portable device, the first portion being laterally wider than the connector portion but having a lateral width less than the second section, and a bottom end of the connector portion being located adjacent an intersection between the heart apex mitral-covering first section and the second section.

10. The device according to claim 1, wherein the heart apex mitral-covering first section is laterally longer than the second section of the second portion, all of the electrodes of the second portion are laterally spaced from each other, and the heart apex mitral-covering first section of the second portion has a substantially constant vertical dimension adjacent the electrodes of the second portion.

11. The device according to claim 1, wherein the second section is oriented at an offset angle with respect of the heart apex mitral-covering first section of the second portion.

12. The device according to claim 11, wherein the angle is from about 15° to 35°.

13. The device according to claim 1, wherein the first and second portions of the device comprise flexible regions.

14. The device according to claim 1, further comprising a pulse oximeter, located on an opposite side of the second portion from the at least three ECG electrodes with the wireless communicator therebetween, configured to monitor an oxygen saturation level from a region proximal to the heart of the user.

15. The device according to claim 1, wherein the temperature sensor is configured to monitor a temperature from a region proximal to the heart of the user, the temperature sensor is located vertically lower than at least one of the at least two ECG electrodes, and the temperature sensor is laterally located closer to the vertical line than are the at least three ECG electrodes.

16. The device according to claim 1, further comprising an accelerometer located below a horizontal line extending through an uppermost of the at least two ECG electrodes of the first portion and above a horizontal line extending through a lowermost of the at least three ECG electrodes of the second portion.

17. The device according to claim 1, wherein the first portion is encapsulated in an over-molded material.

18. A method of manufacturing a portable device for measuring electrocardiographic signals, the method comprising:
    forming a first portion comprising at least two ECG electrodes that are vertically higher than any other electrode of the device;
    forming a second portion comprising a horizontally elongated longer section and a horizontally elongated shorter section, the longer section comprising at least three ECG electrodes, all of the ECG electrodes of the longer section being laterally spaced apart from each other and located laterally outboard of the ECG electrodes of the first portion, and the longer and shorter sections being lower than the first portion;
    locating a wireless communicator adjacent an intersection between the longer and the shorter sections;
    encapsulating a waterproof casing that encloses the first portion;
    connecting a single chest encircling strap to only the longer and shorter sections below the ECG electrodes of the first portion to cause all of the electrodes to be in heart signal electrical flow locations;
    assisting in generating ECG waveforms with a controller to take:
        (a) a first potential difference measurement using one of the electrodes of the first portion and one of the electrodes of the second portion;
        (b) a second potential difference measurement using one other of the electrodes of the first portion and one other of the electrodes of the second portion; and
        (c) a third potential difference measurement using one other of the electrodes of the first portion and one other of the electrodes of the second portion;
    the controller simultaneously taking the first, second and third potential difference measurements at three independent user body positions; and
    a layout of electrodes on the portable device being configured to cause the first portion of the device to be located superficially at a sinoatrial node of a heart of the user's body when the second portion is located superficially at an apex mitral area of the heart of the user's body.

19. The method of claim 18, further comprising a lung or heart temperature monitor located between a pair of the at least two ECG electrodes or between a pair of the at least three ECG electrodes.

20. The method of claim 18, further comprising creating the horizontally elongated longer section of the second portion to have continuously curved upper and lower edges, creating the horizontally elongated shorter section to be offset angled from the longer section at the intersection, and creating a substantially constant width dimension of the longer section between lateral ends thereof.

21. A portable device for measuring electrocardiographic signals, the device comprising:
    (a) an uppermost portion comprising two ECG detectors configured to cover a sinoatrial node of a user, the two ECG detectors being vertically higher than any other detector of the device;
    (b) a lowermost portion elongated in a substantially horizontal direction and being located below the uppermost portion, comprising:
        (i) a heart apex mitral-covering first section comprising at least three ECG detectors, which are electrodes; and
        (ii) a second section comprising a detector;
    (c) a controller assisting to generate ECG waveforms with input from:
        (i) a first potential difference measurement using one of the detectors of the uppermost portion and one of the detectors of the lowermost portion;
        (ii) a second potential difference measurement using one other of the detectors of the uppermost portion and one other of the detectors of the lowermost portion; and
        (iii) a third potential difference measurement using the one other of the detectors of the uppermost portion and a further one other of the detectors of the lowermost portion;
    (d) a waterproof casing encapsulating the uppermost portion; and
    (e) a single user removably attaching the detectors in operating positions with all of the ECG detectors being located where heart electrical signals flow, the single strap being a chest strap connected to only the lowermost portion.

22. The device of claim 21, wherein the at least three ECG detectors of the heart apex mitral-covering first section comprises four ECG detectors, which are electrodes; wherein the heart apex mitral-covering first section is laterally longer than the second section.

23. The device of claim 22, further comprising an accelerometer located below a horizontal line extending through an uppermost of the at least two ECG detectors of the uppermost portion and above a horizontal line extending through a lowermost of the at least three ECG detectors of the lowermost portion.

24. The device of claim 21, wherein the heart apex mitral-covering section of the lowermost portion is longer than the second section of the lowermost portion, the heart apex mitral-covering section has a continuously curved upper edge, the sections of the lowermost portion are offset angled from each other at an intersection of the sections, and the uppermost portion is located above a horizontal line through the sections and the strap.

25. The device of claim 21, wherein the detector on the second section is a pulse oximeter.

26. The device of claim 21, further comprising a temperature sensor located vertically lower than at least one of the ECG detectors of the at least two ECG detectors and the at least three ECG detectors, and the temperature sensor is laterally located closer to a vertically elongated centerline than are the at least three ECG detectors.

* * * * *

UNITED STATES PATENT AND TRADEMARK OFFICE
CERTIFICATE OF CORRECTION

| | |
|---|---|
| PATENT NO. | : 11,647,929 B2 |
| APPLICATION NO. | : 15/841719 |
| DATED | : May 16, 2023 |
| INVENTOR(S) | : Rameen Shakur |

It is certified that error appears in the above-identified patent and that said Letters Patent is hereby corrected as shown below:

In the Claims

In Column 10, Claim 21, Line 46, delete "user" and insert -- strap --.

Signed and Sealed this
Eleventh Day of July, 2023

Katherine Kelly Vidal
Director of the United States Patent and Trademark Office